United States Patent [19]
Lombardi

[11] Patent Number: 5,120,299
[45] Date of Patent: Jun. 9, 1992

[54] INTRA-AORTIC BALLOON ASSEMBLY WITH HEMOSTASIS DEVICE

[75] Inventor: Edward J. Lombardi, Derry, N.H.

[73] Assignee: Kontron Instruments, Inc., Everett, Mass.

[21] Appl. No.: 610,285

[22] Filed: Nov. 7, 1990

Related U.S. Application Data

[63] Continuation-in-part of Ser. No. 53,183, May 22, 1987.

[51] Int. Cl.⁵ .............................................. A61B 19/00
[52] U.S. Cl. ..................................................... 600/18
[58] Field of Search .................. 600/18; 604/158, 159, 604/162, 53

[56] References Cited

U.S. PATENT DOCUMENTS

| | | | |
|---|---|---|---|
| 3,921,631 | 11/1975 | Thompson | 604/53 |
| 4,473,067 | 9/1984 | Schiff | 600/18 |
| 4,738,658 | 4/1988 | Magro et al. | 604/53 |
| 4,850,960 | 7/1989 | Grayzel | 604/53 |
| 4,883,461 | 11/1989 | Sawyer | 604/53 |
| 4,897,077 | 1/1990 | Cicciu et al. | 600/18 |

*Primary Examiner*—William E. Kamm
*Attorney, Agent, or Firm*—Morgan & Finnegan

[57] ABSTRACT

An intra-aortic balloon assembly which includes an hemostasis device slidably mounted to a balloon catheter, and method for percutaneous insertion of such assembly. The hemostasis device provides a distal constant diameter segment dimensioned to minimize initial resistance to the insertion of the hemostasis device, integrated with a second proximal segment of larger constant diameter via a transition segment. The second constant diameter segment is proportioned to fill the opening in the patient's skin created by the insertion of the intra-aortic balloon and thereby stop any bleeding from the femoral artery at the insertion site. The method includes the steps of (1) percutaneously inserting the intra-aortic balloon into the femoral common artery, with or without the use of a tear-away insertion sheath, (2) removing the insertion sheath (if one is used) after insertion of the intra-aortic balloon assembly, and (3) inserting the hemostasis device into the patient's skin at the insertion site to stop bleeding which may occur upon sheathless insertion of the wrapped balloon or removal of the insertion sheath.

11 Claims, 4 Drawing Sheets

INTRA-AORTIC BALLOON ASSEMBLY WITH HEMOSTASIS DEVICE

CROSS-REFERENCE TO RELATED APPLICATION

This is a continuation-in-part to U.S. patent application Ser. No. 53,183 filed May 22, 1987, the disclosure of which is hereby incorporated by reference hereinto.

BACKGROUND AND OBJECTS OF THE INVENTION

The present invention relates generally to intra-aortic balloon (hereinafter "IAB") assemblies, and more particularly, to an improved IAB assembly and percutaneous method for inserting same employing a new hemostasis device to facilitate insertion of the IAB into the body by (1) reducing insertion time, and (2) by lowering the degree of obstruction in the femoral artery, while at the same time controlling bleeding back through the insertion site.

IAB devices are introduced into the body and are used to assist the pumping action of the heart. See, for example, U.S. Pat. No. 4,362,150. In some instances, they may remain in the body for extended periods of time, such as several days or more.

One method of installing an IAB device in the body is via non-surgical insertion into the femoral common artery using the percutaneous "Seldinger" insertion technique. In the Seldinger technique, the skin is punctured with a hypodermic needle to form a hole through the skin and into the femoral artery. A first guide wire is inserted through the needle into the femoral artery and the needle is then removed from the artery, leaving the guide wire in place. The puncture hole created by the needle is then expanded by an inserter dilator (for example, an 8-French dilator) which slides over the guide wire through the skin and into the artery. The inserter dilator is then removed and a series of progressively larger dilators are inserted into the hole over the guide wire to increase the size of the hole. Next, an insertion sheath is passed through the hole over the guide wire and into the femoral artery. This sheath has an inside diameter generally corresponding to the outside diameter of the IAB to be inserted. The first guide wire is removed and replaced by a second guide wire which is fed up through the artery to the vicinity of the aortic arch. The IAB is passed over this second guide wire and slides up through the insertion sheath and along the artery to a point just below the aortic arch.

Although the foregoing procedure generally is a safe, rapid and efficacious way of intra-aortic balloon insertion, the prerequisite insertion of the sheath requires time and equipment to perform, often under circumstances such that time is a critical factor to patient survival, as during cardiogenic shock. During the foregoing procedure, arterial bleeding through the insertion sheath must be carefully controlled during the time interval between the removal of the first guide wire from the sheath and the insertion of the wrapped balloon containing the second guide wire. Often, especially in a hypovolemic patient, this loss of blood may be critical.

Moreover, when the balloon bladder is wrapped around the central cannula, spiral interstices are produced along its length. The interstices of the wrapped balloon membrane do not provide for the complete occlusion of the insertion sheath between its inner wall and the wrapped balloon. Therefore, a certain amount of arterial bleeding takes place during the time that is required to fully insert the wrapped balloon membrane portion of the balloon catheter into the blood vessel. In some cases, the insertion sheath may have to be withdrawn partly from the percutaneous wound to permit complete introduction of the balloon membrane into the sheath, especially in those cases of extreme vascular tortuosity. This creates an additional loss of critical time and of critical blood.

Another problem experienced with some patients is that after IAB insertion is complete, blood flow to the lower extremities is diminished substantially. The decrease in blood flow is generally attributable to the obstruction of the femoral artery caused by the relatively large diameter of the insertion sheath extending into the artery. By removing the sheath, the obstruction in the femoral artery can be decreased substantially. Certain prior art techniques attempt to solve this problem by utilizing splittable ("tear-away") insertion sheaths, such as, for example, those identified in U.S. Pat. Nos. 4,166,469, 4,581,019 and 4,581,025. Once the insertion sheath is removed, however, the arterial wall must constrict to seal around the balloon catheter (which has a smaller outside diameter than the insertion sheath) to prevent bleeding at the insertion site. In nonelastic or diseased vessels, the required vessel constriction may not always occur resulting in profuse bleeding at the insertion site between the IAB catheter and arterial puncture. If bleeding cannot be stopped, the IAB must be removed. One way to stop this bleeding is to exert pressure on the artery above the insertion site. Such an approach, however, adds an additional step to the IAB insertion process, and may also result in damage to the balloon catheter.

In response to the foregoing problems, other approaches have been advanced involving the use of a tapered hemostasis device which is slidably mounted to the balloon catheter, and which can be inserted into the patient after the tear-away sheath is removed to control bleeding at the insertion site. See, for example, the device's identified in my co-pending U.S. patent application Ser. No. 53,183 and Magro et al. U.S. Pat. No. 4,738,658. The subject invention is an improvement over those devices. For example, due to the structure of such devices, a patient having limited or little vessel and skin elasticity will ordinarily require a greater length of the hemostasis device to be inserted to stop bleeding at the IAB puncture site than a patient whose vessels and skin are relatively elastic. As the length and diameter of the hemostasis device inserted increases, there will be an accompanying increase in both insertion time and body resistance to insertion.

Accordingly, it is an object of the present invention to provide a new IAB assembly and method of inserting same into the body which incorporates a new hemostasis device for controlling bleeding at the insertion site after insertion of the IAB. It is another object of the present invention to provide a new IAB assembly including a hemostasis device which can be inserted into the patient using either a tear-away insertion sheath or a sheathless insertion technique.

It is yet a further object of the present invention to provide a new hemostasis device which controls bleeding at the IAB insertion site without restricting good blood flow through the femoral artery to any great degree. It is still another object of the invention to provide a new IAB assembly including a hemostasis device which does not rely on a tapered configuration to perform the hemostasis function.

It is still another object of the invention to provide a new hemostasis device providing a first constant diameter segment at the distal end thereof configured and dimensioned to generate less initial resistance during insertion into the patient's skin, and a second constant diameter segment positioned proximally with respect to the first segment which is dimensioned to fill the opening in the patient's skin created by the insertion of the IAB device, and thereby stop bleeding from the femoral artery at the insertion site.

It is still a further object of the present invention to provide a new hemostasis device including a transition segment connecting the first and second constant diameters segments which allows essentially immediate transition from the first segment to the second segment during insertion of the hemostasis device, yet at the same time minimizes any resistance encountered during insertion of the second larger diameter segment through the patient's skin.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvement herein shown and described.

SUMMARY OF THE INVENTION

Briefly described, the present invention comprises an IAB assembly and method for inserting same into the body in which the assembly incorporates a hemostasis device slidably mounted to the balloon catheter for controlling bleeding from the insertion site after insertion of the IAB.

According to one specific aspect of the invention, the hemostasis device is formed with a first constant diameter segment at the distal end thereof which is only slightly larger in diameter than the outside diameter of the balloon catheter, and which is dimensioned to be as small as possible so as to pass through the opening made by the passage of the balloon bladder through the percutaneous insertion site and into the femoral artery.

According to another specific aspect of the invention, the first segment of the hemostasis device is integrated with a second constant diameter segment positioned proximally with respect thereto via a transition segment. As preferably embodied, the second constant diameter segment is proportioned to fill the opening in the patient's skin at the percutaneous insertion site upon slidable insertion of the hemostasis device thereinto, and thereby stop bleeding from the femoral artery at the insertion site. According to the invention, the transition segment is configured and dimensioned so as to allow essentially immediate transition from the first segment to the second segment during insertion of the hemostasis device, yet at the same time minimize any resistance encountered during insertion of the larger diameter second segment through the patient's skin.

As here embodied, the inside diameter of the hemostasis device is sized to provide a close clearance between the inside of the hemostasis device at its distal end and the outside of the balloon catheter. Preferably, the inside diameter of the hemostasis device should be sized so as to maintain this close tolerance, yet at the same time permit the sheath to be easily slidably translated along the balloon catheter to and from the percutaneous insertion site.

According to another specific aspect of the invention, the hemostasis device is provided with a cuff member releasably attachable to the proximal end thereof to prevent any residual backflow of blood from spurting out of the sheath while it is being inserted into the femoral artery. According to another specific aspect of the invention, the hemostasis device can be used in conjunction with an IAB apparatus inserted into the patient using either a tear-away insertion sheath or using a sheathless insertion technique.

It will be appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part thereof, illustrate preferred embodiments of the invention and, together with the detailed description, serve to explain the principles of the invention.

DESCRIPTION OF THE PREFERRED EMBODIMENTS

Referring now to the accompanying drawings wherein like reference characters refer to like parts throughout the various views, there is shown in FIG. 1 lines (a-d) the various steps employed in the Seldinger technique for inserting an IAB device percutaneously, and in FIGS. 2a through 6, the preferred embodiments of the IAB assembly with hemostasis device and method for percutaneous insertion of same according to the present invention.

Referring first to FIGS. 1 lines (a–d), FIG. 1 line (a) shows puncture of the skin and the femoral artery using a Seldinger needle. FIG. 1 line (b) shows placement of a guide wire 5 into the artery through the hollow bore of the needle. FIG. 1 line (c) shows removal of the hypodermic needle from the artery leaving the guide wire 5 in place. Finally, FIG. 1 line (d) shows placement of an insertion sheath into the artery over the guide wire following dilation of the insertion site.

Figure 1A:
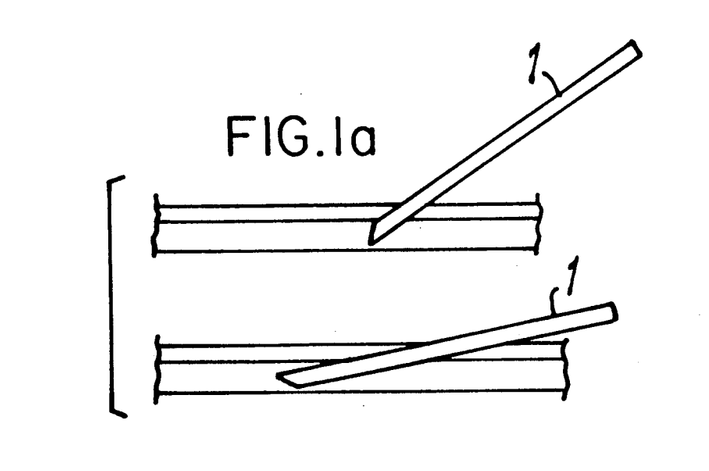
FIG. 1 lines (a-d) shows in succession, the Seldinger technique steps of (a) puncturing the skin and artery with a hypodermic needle, (b) inserting a guide wire through the needle, (c) removing the needle leaving the guide wire in place, and (d) placing an insertion sheath into the artery following dilation of the puncture site.
Figure 1B:
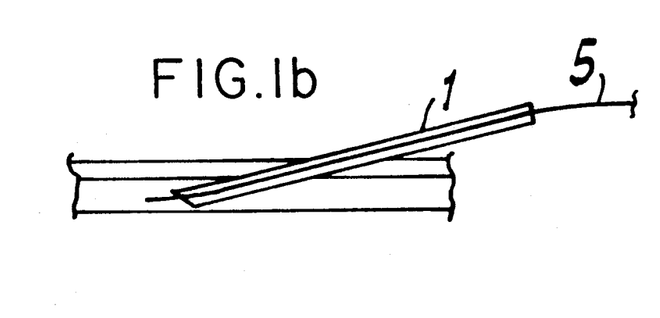
Figure 1C:
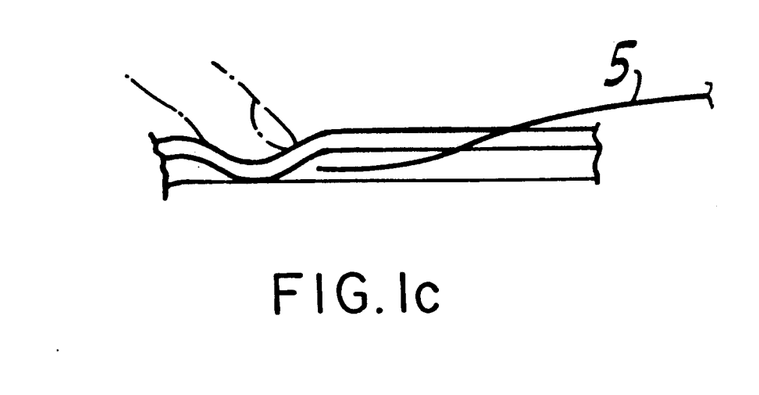
Figure 1D:
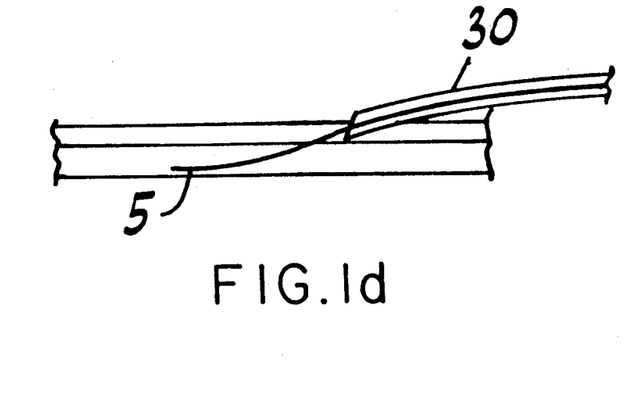
Figures 2A, 2B:
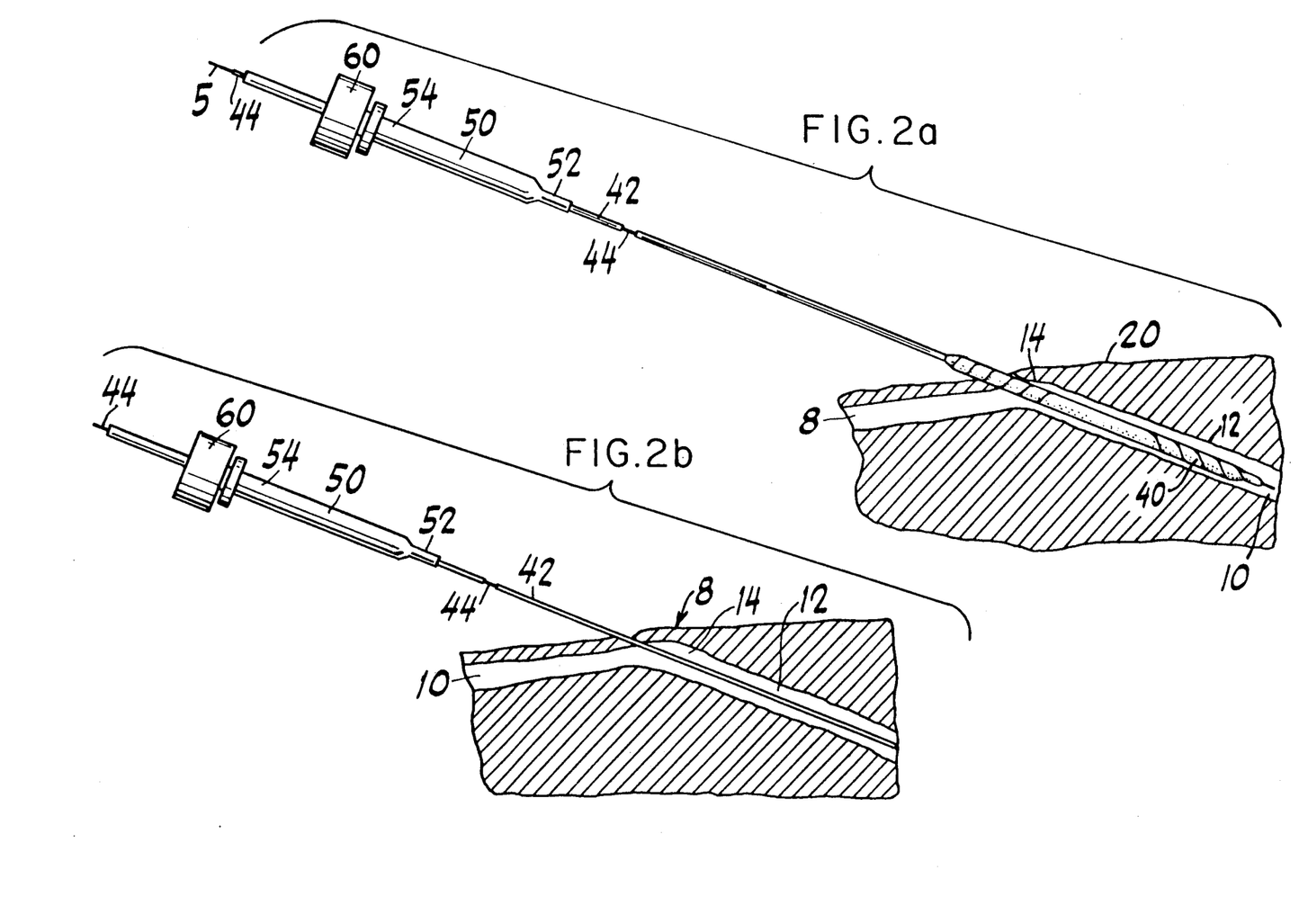
FIG. 2a is a side elevation view of an IAB device according to the present invention showing the IAB bladder being directly inserted into the femoral common artery without an insertion sheath.
FIG. 2b is a side elevation view partly in cross-section showing the IAB device of FIG. 1 following insertion of the IAB bladder into the femoral common artery.
Figure 5:
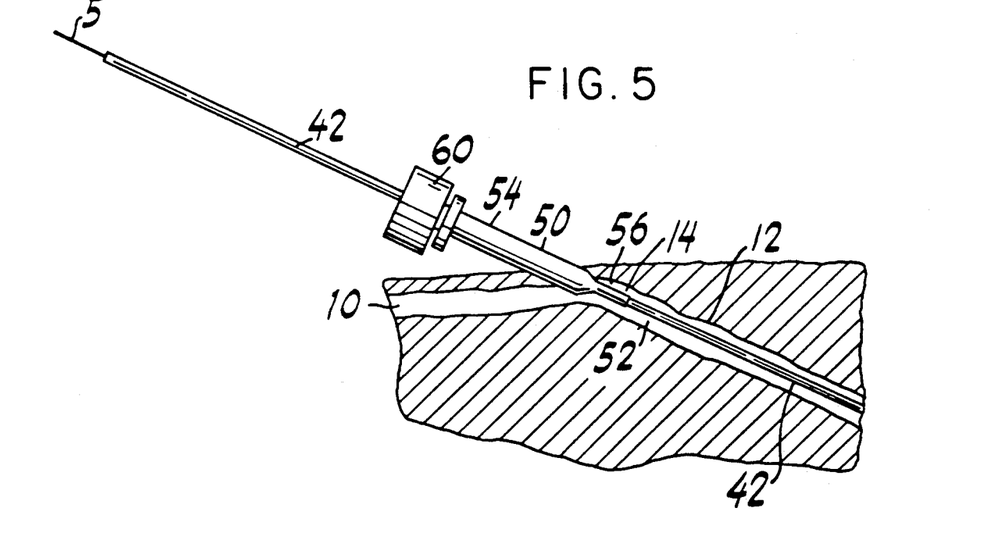
FIG. 5 is a side elevation view of the IAB device of FIGS. 2a, 2b, 3 and 4 showing the hemostasis device of the present invention positioned within the insertion puncture in accordance with the IAB insertion methods of the present invention illustrated in FIGS. 2a, 2b, 3 and 4.

Referring now to FIGS. 2a, 2b, and 5, there is shown the insertion of an IAB assembly with hemostasis device according to the invention into a femoral common artery through the skin using a new percutaneous insertion technique also according to the invention. With reference to these figures, a physician (not shown) would be positioned in the left-hand margin in relation to the various elements being described. The terms "proximal" and "distal" as used herein shall refer to position a relative to that of the physician.

Referring particularly to FIGS. 2a and 2b, the IAB assembly comprises and IAB bladder 40 which is attached to a balloon catheter 42. The IAB is a double lumen device with a central cannula 44 preferably of, but not limited to, the type described in U.S. Pat. No. 4,362,150, which patent is incorporated herein by reference. The IAB can have a wrap handle for rotation as described in the above patent or can have a fixed type configuration.

Prior to insertion, the bladder 40 is wrapped about itself to reduce its diameter either by the manufacturer or by the physician. As will be recognized by those skilled in the art, the balloon catheter 42 may be attached at its proximal end to a rotating or fixed handle (not shown) and may also be connected in known manner to an intra-aortic balloon pumping/monitoring system (also not shown).

Figure 6:
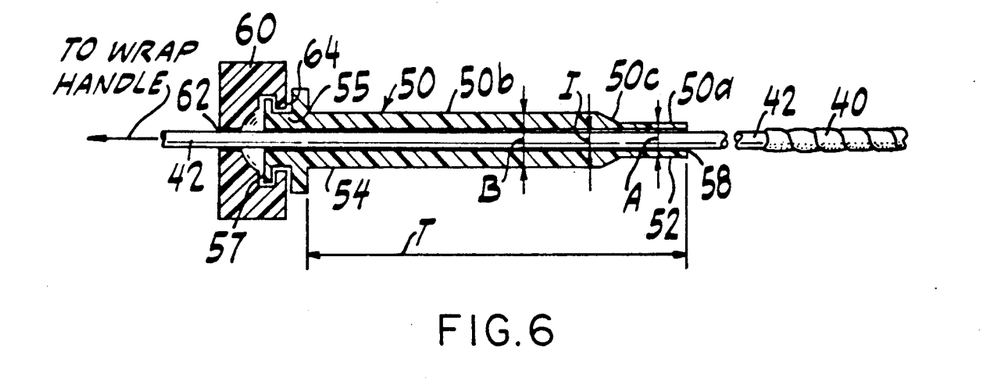
FIG. 6 is a cross-section of the hemostasis device according to the invention showing the hemostasis device installed on a balloon catheter.

Referring now to FIG. 6, there is shown a preferred embodiment of hemostasis device 50 in accordance with the present invention. As shown in FIG. 6, hemostasis device 50 is slidably mounted to balloon catheter 42 and generally comprises a the distal end of the device, a second segment 50b positioned proximally with respect to first segment 50a and formed with a neck portion 55, a transition segment 50c connecting segments 50a and 50b together, a flange 57 formed on segment 50b at the proximal end of the hemostasis device, and a cuff 60 releasably connectable to flange 57. As preferably embodied, the hemostasis device is manufactured from a resilient plastic material, such as polytetrafluoroethylene (Teflon ®) or polyethylene. According to the invention, the cuff 60 is manufactured from an elastomeric material such as, for example, Kraton; although no particular elastomeric material is preferred.

As preferably embodied, first segment 50a has a constant outside diameter which is only slightly larger than the outside diameter of catheter 42, and which is dimensioned to be as small as possible so as to pass through the opening made by the passage of balloon bladder 40 through the percutaneous insertion site and into the femoral artery. For example, in a preferred embodiment of the invention wherein the outside diameter of the balloon catheter is about 10.5 French (i.e. about 0.138 inches), the outside diameter (A) of segment 50a (see FIG. 6) is about 0.150 inches. Similarly, for a 9.5 French balloon catheter (i.e. about 0.128 inches in diameter), the outside diameter (A) of segment 50a is about 0.142 inches. As here embodied, segment 50a preferably has a length of at least about ⅛ inch, and is configured and dimensioned to generate less initial resistance during insertion through the patient's skin so that the hemostasis device as a whole can be more easily inserted into the patient. Although the overall resistance to further insertion will increase as larger diameter segment 50b of the hemostasis device (described below) is inserted, the safe passage of segment 50a through the skin will avoid the danger of collapsing or buckling of the hemostasis device at its distal end.

To control bleeding at the insertion site during and after insertion of the balloon bladder, hemostasis device 50 of the present invention is provided with a second segment 50b connected to segment 50a via a transition segment 50c. As preferably embodied, segment 50b has a constant outside diameter dimensioned to be larger than the outside diameter of the wrapped balloon 40. This will enable segment 50b to fill the opening in the patient's skin created by the insertion of balloon 40 into the patient's femoral artery and thereby stop bleeding from the femoral artery at the insertion site. As here embodied, the outside diameter of segment 50b is preferably about 0.169 inches. This will provide adequate hemostasis capability for all commercially available IAB assemblies; the largest being a 50 cc assembly wherein the outside diameter of the wrapped balloon is about 0.162 inches.

According to the invention, transition segment 50c is configured and dimensioned so as to allow essentially immediate transition from first segment 50a to second segment 50b during insertion of hemostasis device 50 into the percutaneous insertion site opening, yet at the same time minimize any resistance encountered during insertion of larger diameter segment 50b through the patient's skin. As preferably embodied, transition segment 50c has a tapered configuration and a length of about ⅛ inch measured linearly from the end of segment 50a to the beginning of segment 50b. Although the angle of taper for segment 50c will vary in accordance with the dimensions of segments 50a and 50b employed, it is preferred that transition segment 50c be tapered in a manner so as to provide the smoothest and quickest transition from first segment 50a to second segment 50b during the insertion process. Because transition segment 50c does not perform a hemostasis function, it may, in accordance with the invention, be omitted from the hemostasis device structure (with second segment 50b immediately following first segment 50a). Such an arrangement, however, is less preferred as it will result in increased resistance to insertion of the hemostasis device into the patient.

As preferably embodied, the length of segment 50b is about 2.75 inches, thereby giving hemostasis device 50 an overall length (T) between distal end 52 and proximal end 54 of preferably about 3.0 inches. Advantageously, because the combined length of hemostasis device entering the patient prior to segment 50b is on the order of only about ¼ of an inch (i.e. the combined length of first segment 50a and transition segment 50c), obstruction to continued blood flow along the femoral artery caused by the insertion of the hemostasis device, as well as the body's resistance to insertion of the hemostasis device, will both be minimized.

As here embodied, the inside diameter (I) of hemostasis device 50 can be about the same throughout its entire length (as shown in FIG. 6), or can vary in accordance with the configuration of the outside of hemostasis device 50. In any event, the inside diameter of device 50 is preferably sized to provide a close clearance 58 between the inside of the hemostasis device 50 at distal end 52 and the outside of the balloon catheter 42. Preferably, the inside diameter (I) of hemostasis device 50 at distal end 52 is between about 2 to 3 thousandths of an inch larger than the outside diameter of the balloon catheter 42 to allow for manufacturing tolerance. For example, in a preferred embodiment of the invention wherein the outside diameter of the balloon catheter is about 10.5 French (i.e., about 0.138 inches), the inside diameter (I) of the hemostasis device 50 at the distal end 52 is about 0.140 inches to provide a clearance 58 of about 0.002 inches between the hemostasis device and the catheter.

More preferably, in view of the resilience of the materials utilized, one can maintain an interference fit between balloon catheter 42 and hemostasis device 50 such that the inside diameter (I) of the hemostasis device is essentially the same as the outside diameter of the balloon catheter. This close fit clearance 58 permits the outside diameter of hemostasis device 50 to be as small as possible at the distal end 52 with the balloon catheter 42 providing structural support for the hemostasis device 50 during insertion to prevent an accordion effect from occurring at distal end 52. Advantageously, the resilient, low-friction nature of the hemostasis device material allows the device to be easily slidably advanced along the catheter in either a distal or proximal direction substantially without loosening the interference fit between the parts.

According to the invention, hemostasis device 50 is provided at its proximal end with a neck 55 and flange 57, each formed on second segment 50b. As here embodied, neck 55 and flange 57 are held within a cuff member 60. As shown in FIG. 6, cuff 60 is sized to provide a close clearance 64 between the cuff and neck 55 of the hemostasis device. Additionally, cuff 60 is sized to provide a close clearance 62 between the cuff and balloon catheter 42. In this manner, cuff 60 is able to seal the proximal end of hemostasis device 50 against backflow of blood through the device after it has been inserted into the femoral artery. Close clearance 62 also precludes slippage of cuff 60 and, in turn, hemostasis device 50 along catheter 42 due to arterial pressure and the like.

Operation of the hemostasis device 50 is relatively straightforward. An insertion technique according to the invention using the hemostasis device will now be described. Referring to FIG. 2a, a small hypodermic needle (not shown) is inserted through the skin 20 of a patient to perforate or puncture the femoral artery 10. When blood spurts from the open external end of the needle, placement of the hypodermic needle within the artery 10 is confirmed. A guide wire 5 sufficient in length to reach the central aorta (e.g. up to about 170–190 cm or longer) is fed into the artery 10 by passing the guide wire through the center of the hollow hypodermic needle.

Next, the hypodermic needle is removed leaving the guide wire 5 in place. One or more progressively larger dilators (preferably a single expanding, e.g. Grunzig type dilator) is then placed over the guide wire and advanced through the perforated skin 20 and into the artery 10 in order to expand the hole to achieve an opening large enough to permit the passage of the wrapped IAB bladder 40. For example, when using a 10.5 French IAB the hole should be dilated to approximately 10 French in diameter. Once the skin 20 and artery 10 have been fully dilated, the dilator is removed and the IAB device is inserted directly into the patient without passing it through an insertion sheath.

Still referring to FIG. 2a, the IAB bladder 40 in its wrapped condition has a larger outside diameter than the IAB catheter 42. As a result, the IAB bladder 40 will dilate the insertion site to a larger diameter than that of the catheter 42. As can be seen in FIG. 2b, after passage of the IAB the insertion site 8 may have an opening which, due to some inelasticity in the skin, has not completely closed around the catheter 42. This condition may result in uncontrollable bleeding from the insertion site.

As a means to diminish bleeding when it occurs, hemostasis device 50 is slidably advanced in a distal direction along catheter 42 so as to insert first segment 50a thereof into opening 14 in the wall of femoral artery 10 made by passage of the IAB balloon bladder thereinto. Hemostasis device 50 is further advanced into the femoral artery until segment 50b thereof fills opening 14 (see FIG. 5). In this position, the outside diameter of segment 50b will sufficiently fill opening 14 so as to provide elastic, sealing contact between the skin opening and segment 50b, and thereby stop bleeding which might have resulted after insertion of the IAB device. The configuration and dimensions of the hemostasis device (described above) control bleeding without restricting good blood flow through artery 10 to any great degree. Moreover, any residual backflow of blood up through device 50 during the insertion process will be prevented from spurting out of the hemostasis device via cuff member 60.

Figures 3, 4:
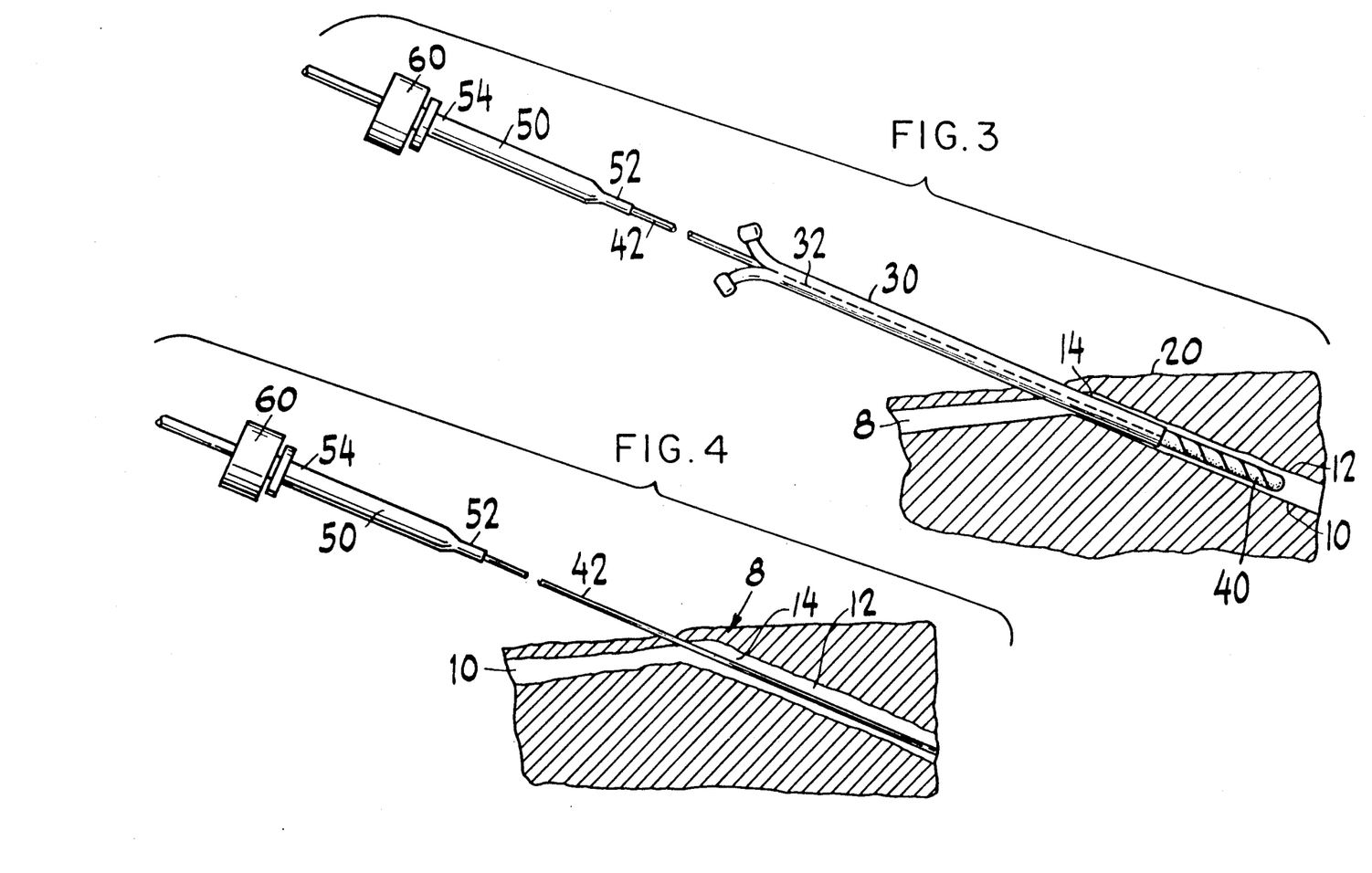
FIG. 3 is a side elevation view of an IAB device according to the present invention showing the IAB bladder being inserted into the femoral common artery using an insertion sheath.
FIG. 4 is a side elevation view partly in cross-section showing the IAB device of FIG. 3 following insertion of the IAB bladder into the femoral common artery.

Referring now to FIGS. 3–5, an alternative IAB insertion technique according to the invention using a tear-away insertion sheath will now be described. FIG. 3 shows, from left to right, a hemostasis device 50 slidably connected to a balloon catheter 42, a tear-away insertion sheath 30, an IAB bladder 40, and a femoral common artery 10. As shown in FIG. 3, an IAB device is inserted into the femoral common artery 10 through skin 20 using the percutaneous Seldinger technique. Prior to insertion, bladder 40 is wrapped about itself to reduce its diameter. The balloon catheter 42 may be attached at its proximal end to a wrap handle (not shown) and may also be connected to an intra-aortic balloon pumping/monitoring system (also not shown).

Next, a tear-away insertion sheath 30 is inserted into artery 10 through opening 14. The tear-away insertion sheath 30 may have a tear line 32 which permits sheath 30 to be torn therealong and removed from insertion site 8 once the balloon 40 has been inserted into the aorta. Alternatively, insertion sheath 30 may be formed by linear extrusion (as is known in the art) to facilitate tearing thereof for removal purposes.

After placement of tear-away insertion sheath 30, an intra-aortic balloon 40 is passed through the insertion sheath and into artery 10 using the following percutaneous insertion (Seldinger) technique. First, a small hypodermic needle (not shown) is inserted through the skin 20 of a patient to perforate or puncture the artery 10. When blood spurts from the open external end of the needle, placement of the hypodermic needle within artery 10 is confirmed. A guide wire (also not shown) is fed into the artery 10 by passing the guide wire through the center of the hollow hypodermic needle. The hypodermic needle is then removed leaving the wire in place.

Next, a dilator (also not shown) is placed over the guide wire and advanced through the perforated skin 20 and into artery 10 in order to dilate (that is enlarge) the artery 10 and create opening 14. The dilator is then removed and a series of larger dilators (not shown) are then fed over the guide wire and into artery 10 to continue the dilation procedure. Once the artery 10 has been fully dilated, the insertion sheath 30 is inserted through the opening 14 and into the artery and the last dilator is removed leaving the insertion sheath 30 extending through the opening 14 and available for insertion of the IAB device over the guide wire and into the patient without requiring surgery.

Once the balloon bladder is inserted into the femoral artery and up into the aorta, the tear-away insertion sheath 30 is removed. Upon removal of the insertion sheath, however, the wall of the femoral artery may not completely constrict around the balloon catheter 42 resulting in uncontrolled bleeding at the insertion site. In order to control such bleeding, the hemostasis device 50 is slid down the balloon catheter 42 towards insertion site 8 and partially into the opening 14.

As discussed above, hemostasis device 50 is inserted into the opening 14 in the wall of artery 10 until the outside diameter of segment 50b fills opening 14 (see FIG. 5). In this position, elastic sealing contact is provided between the patient's skin opening and segment 50b, thereby preventing bleeding at the insertion site without restricting good blood flow through the artery 10 to any great degree. Any residual backflow of blood up through hemostasis device 50 during the insertion thereof will be prevented from spurting out of the hemostasis device 50 via cuff member 60.

It will be appreciated by those skilled in the art that the present invention in its broader aspects is not limited to the particular embodiments shown and described herein, and that variations may be made which are within the scope of the accompanying claims without departing from the principle of the invention and without sacrificing its chief advantages.

What is claimed is:

1. An intra-aortic balloon apparatus comprising:
    a balloon catheter having a proximal end and a distal end;
    an inflatable and deflatable balloon bladder sealidly attached to the distal end of said balloon catheter for percutaneous insertion into the femoral artery of patient;
    a hemostasis device having a proximal end and a distal end, said hemostasis device slidably mounted to said balloon catheter between said balloon bladder and said proximal end of said balloon catheter, said hemostasis device including:
    i) a first segment formed at said distal end of said hemostasis device having a constant outside diameter, said first segment being of a dimension which is as small as possible so as to pass through the opening made by the passage of said balloon bladder through the percutaneous insertion site and into said femoral artery;
    ii) a second segment for insertion into said percutaneous insertion site opening positioned proximally with respect to said first segment, said second segment having a constant diameter larger than the outside diameter of said first segment and being of a dimension so as to fill said opening to stop any bleeding from said femoral artery at said insertion site, yet permit blood flow along said femoral artery;
    iii) a transition segment connecting said first segment to said second segment, said transition segment having a dimension so as to allow essentially immediate transition from said first segment to said second segment during insertion of said hemostasis device into said percutaneous insertion site opening, yet at the same time minimize any resistance encountered during the insertion of said second segment through the patient's skin;
    iv) said hemostasis device having an inside diameter dimension so as to provide a clearance between the inside of said hemostasis device at said distal end and said balloon catheter of between about 2 to 3 thousandths of an inch; and
    sealing means releasably attached to the proximal end of said hemostasis device for preventing bleeding between said hemostasis device and said balloon catheter after insertion of said balloon bladder and hemostasis device in the patient.

2. An intra-aortic balloon apparatus according to claim 1, wherein said first segment is about one-eighth of an inch in length.

3. An intra-aortic balloon apparatus according to claim 1, wherein said transition segment is about one-eighth of an inch in length.

4. An intra-aortic balloon apparatus according to claim 1, wherein said second segment is about three inches in length.

5. An intra-aortic balloon apparatus according to claim 1, wherein the overall length of said hemostasis device is about four inches.

6. An intra-aortic balloon apparatus comprising:
    a balloon catheter having a proximal end and a distal end;
    an inflatable and deflatable balloon bladder sealidly attached to the distal end of said balloon catheter for percutaneous insertion into the femoral artery of patient;
    a hemostasis device having a proximal end and a distal end, said hemostasis device slidably mounted to said balloon catheter between said balloon bladder and said proximal end of said balloon catheter, said hemostasis device including:
    i) a first segment formed at said distal end of said hemostasis device having a length of about one-eighth of an inch and a constant outside diameter, said first segment being of a dimension which is as small as possible so as to pass through the opening made by the passage of said balloon bladder through the percutaneous insertion site and into said femoral artery;
    ii) a second segment for insertion into said percutaneous insertion site opening positioned proximally with respect to said first segment, said second segment having a constant outside diameter larger than the outside diameter of said first segment and being of a dimension so as to fill said opening to stop any bleeding from said femoral artery at said insertion site, yet permit blood flow along said femoral artery;
    iii) a transition segment connecting said first segment to said second segment having a length of about one-eighth of an inch, said transition segment having a dimension so as to allow essentially immediate transition from said first segment to said second segment during insertion of said hemostasis device into said percutaneous insertion site opening, yet at the same time minimize any resistance encountered during the insertion of said second segment through the patient's skin;

iv) said hemostasis device having an inside diameter dimension so as to provide a clearance between the inside of said hemostasis device at its distal end and said balloon catheter of no more than about 2 to 3 thousandths of an inch; and sealing means releasably attached to the proximal end of said hemostasis device for preventing bleeding between said hemostasis device and said balloon catheter after insertion of said balloon bladder and hemostasis device in the patient.

7. An intra-aortic balloon apparatus according to claim 6, wherein said transition segment is about one-eighth inch in length.

8. An intra-aortic balloon apparatus according to claim 7, wherein said second segment is about three inches in length.

9. An intra-aortic balloon apparatus according to claim 8, wherein the overall length of said hemostasis device is about four inches.

10. A method for percutaneous insertion of an intra-aortic balloon apparatus into a patient's body though a tear-away insertion sheath and into the femoral artery, wherein said intra-aortic balloon apparatus includes a balloon catheter having a proximal end and a distal end, an inflatable and deflatable balloon bladder sealidly attached to the distal end of the balloon catheter, and a hemostasis device slidably mounted to said balloon catheter, said hemostasis device having a first constant outside diameter segment formed at the distal end thereof configured and having a dimension so as to generate less initial resistance during insertion into the patient's skin, said hemostasis device further including a second constant outside diameter segment having a dimension so as to fill the opening in the patient's skin created by insertion of said balloon bladder thereinto to stop bleeding from said femoral artery at the insertion site, said method comprising the steps of:

percutaneously inserting the balloon catheter into the patient's femoral artery through the tear-away insertion sheath;

removing the tear-away insertion sheath from the body after insertion of said intra-aortic balloon apparatus; and sliding said hemostasis device along said balloon catheter into the opening in the patient's skin at the insertion site, and thence into the femoral artery until said second of said hemostasis device fills said opening so as to stop bleeding from the puncture in the femoral artery which may result when said tear-away insertion sheath is removed.

11. A method for sheathless percutaneous insertion of an intra-aortic balloon apparatus into a patient's body and into the femoral artery, wherein said intra-aortic balloon apparatus includes a balloon catheter having a proximal end and distal end, an inflatable and deflatable balloon bladder sealidly attached to the distal end of the balloon catheter, and a hemostasis device slidably mounted to said balloon catheter, said hemostasis device having a first constant outside diameter segment formed at the distal end thereof configured and having a dimension so as to generate less initial resistance during insertion into the patient's skin, said hemostasis device further including a second constant outside diameter segment with a dimension so as to fill the opening in the patient's skin created by insertion of said balloon bladder thereinto to stop bleeding from said femoral artery at the insertion site, said method comprising the steps of:

forming an opening in the patient's skin and into the femoral artery and progressively dilating said opening to increase its size;

inserting said intra-aortic balloon apparatus through said opening and up through the femoral artery to the vicinity of the aortic arch; and sliding said hemostasis device along said balloon catheter into said opening, and thence into the femoral artery until said second segment of said hemostasis device fills said opening so as to stop bleeding from the puncture in the femoral artery which may result when said intra-aortic balloon is inserted thereto.

* * * * *

UNITED STATES PATENT AND TRADEMARK OFFICE
CERTIFICATE OF CORRECTION

PATENT NO. : 5,120,299
DATED : June 9, 1992
INVENTOR(S) : Edward J. Lombardi

It is certified that error appears in the above-identified patent and that said Letters Patent is hereby corrected as shown below:

Column 2, line 43 "vice's" should read --vices--

Column 5, line 46 after "compromise a" insert --proximal end 54, a distal end 52, a first segment 50a formed at--

Column 11, line 32 "though" should read --through--

Column 12, line 12 after "second" insert --segment--

Signed and Sealed this

Twenty-fourth Day of August, 1993

Attest:

BRUCE LEHMAN

*Attesting Officer*     *Commissioner of Patents and Trademarks*